United States Patent [19]

Smith, Jr. et al.

[11] Patent Number: 4,531,836

[45] Date of Patent: Jul. 30, 1985

[54] METHOD OF EMISSION SPECTROANALYSIS

[75] Inventors: Stanley B. Smith, Jr., Westford; Robert G. Schleicher, Winchester; Jon N. Waterman, North Reading, all of Mass.

[73] Assignee: Allied Corporation, Morristown, N.J.

[21] Appl. No.: 473,326

[22] Filed: Mar. 8, 1983

[51] Int. Cl.³ .......................... G01J 3/18; G01N 21/73
[52] U.S. Cl. ..................................... 356/316; 356/334
[58] Field of Search ............... 356/311, 315, 316, 331, 356/334, 306

[56] References Cited

U.S. PATENT DOCUMENTS 4,326,802 4/1982 Smith et al. ....................... 356/316

OTHER PUBLICATIONS

Spillman et al., *Analytical Chemistry*, vol. 48, No. 2, Feb. 1976, pp. 303–311.

*Primary Examiner*—F. L. Evans
*Attorney, Agent, or Firm*—Lowell H. McCarter

[57] ABSTRACT

A spectroanalytical method includes the steps of exciting material to spectroemissive levels, dispersing radiation from the excited sample material into a spectrum, positionally locating a reference constituent of the excited material in the spectrum, the reference constituent having a known wavelength offset from an element of interest in the sample material to be analyzed, and then shifting the known wavelength offset by an essentially hysteresis free mechanism and making an analytical measurement at that wavelength offset position of radiation produced by a spectrum from sample material that has been excited to spectroemissive levels.

11 Claims, 8 Drawing Figures

METHOD OF EMISSION SPECTROANALYSIS

This invention relates to spectroanalytical systems, and more particularly to methods of spectroanalytical analysis that are particularly useful for the analysis of complex spectra.

In spectroanalytical systems, samples to be analyzed may be excited in various ways, for example, by burning the sample in a flame; by placing the sample in an electric arc or spark; or by introducing the sample in a "plasma". Sufficient heating of the sample causes the element of interest to dissociate from its compounds and some of its atoms are "excited" and give off radiation at specific wavelengths. The intensity of such radiation is proportional to the concentration of the element in the sample. The spectra produced by such excitations are frequently complex, particularly when a "plasma" type source is used. In such complex spectra, it is frequently difficult to identify the precise location of the wavelength of interest due to factors such as mechanical error in the scanning system and particular spectral interactions. The system shown in Smith et al., U.S. Pat. No. 4,326,802 employs a technique for locating the wavelength of interest by seeking a spectrum intensity peak in the vicinity of a wavelength of the element of interest. However, at times, that wavelength of interest is masked, for example due to a closely adjacent interfering wavelength peak of another element; or to the masking of a small intensity value of the element of interest by the slope of a closely adjacent interfering signal of greater intensity.

In accordance with the invention, a spectroanalytical method includes the steps of exciting material to spectroemissive levels, dispersing radiation from the excited sample material into a spectrum, positionally locating a reference constituent of the excited material in the spectrum, the reference constituent having a known wavelength offset from an element of interest in the sample material to be analyzed, and then shifting the known wavelength offset by a low hysteresis (essentially hysteresis free) mechanism and making an analytical measurement at that wavelength offset position of radiation produced by a spectrum from sample material that has been excited to spectroemissive levels.

In a particular embodiment, hysteresis free spectrum shifting is accomplished by a refractor plate at the exit slit of a monochromator, but other spectrum shifting mechanisms may be employed such as use of a refractor plate at the monochromator entrance slit, or by a change in monochromator chamber pressure. In a particular embodiment a spectroanalytical system is employed that includes a source of the plasma emission type and a monochromator with a dispersing element of the reflection grating type. The refractor plate at the exit slit of the monochromator is rotated by a stepper motor to shift the spectrum at the rate of 0.01 angstrom per step over a range of two hundred and fifty steps.

This spectroanalysis method is particularly useful in a spectrometer system of the emission type and provides analytical results of enhanced accuracy. Other features and advantages of the invention will be seen as the following description of particular embodiments progresses, in connection with the drawings, in which.

Figure 2:
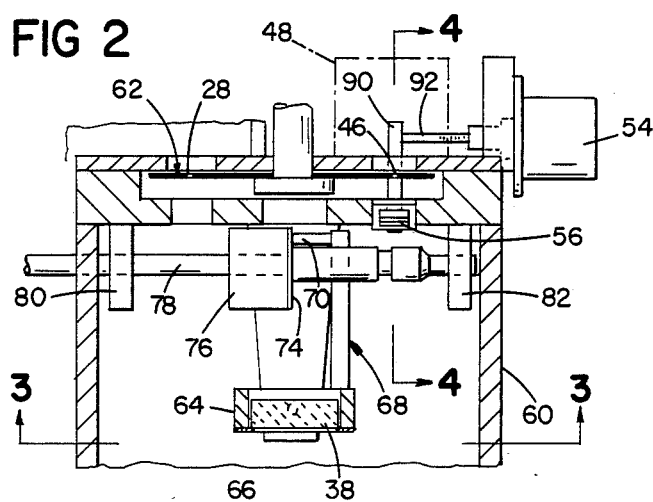
FIG. 2 is a sectional view of portions of the resolving monochromator of the system of FIG. 1 taken along the 2—2 of FIG. 3.
Figure 3:
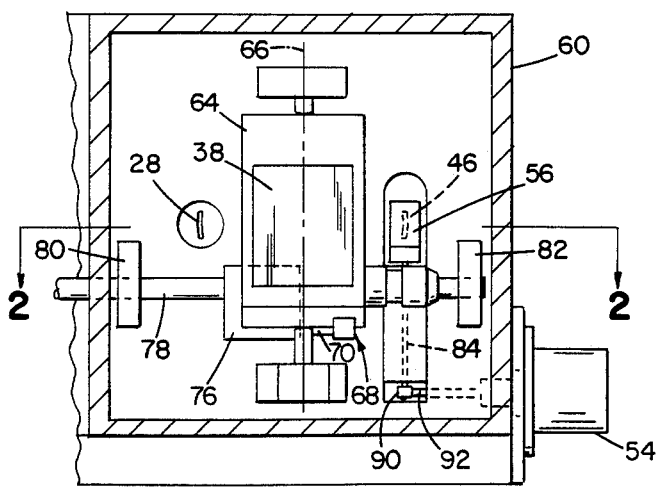
Figure 4:
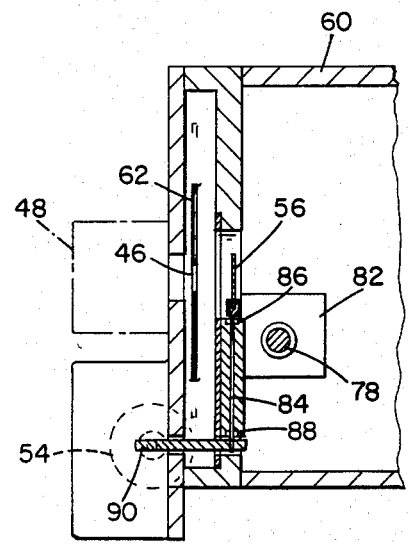
Figure 5:
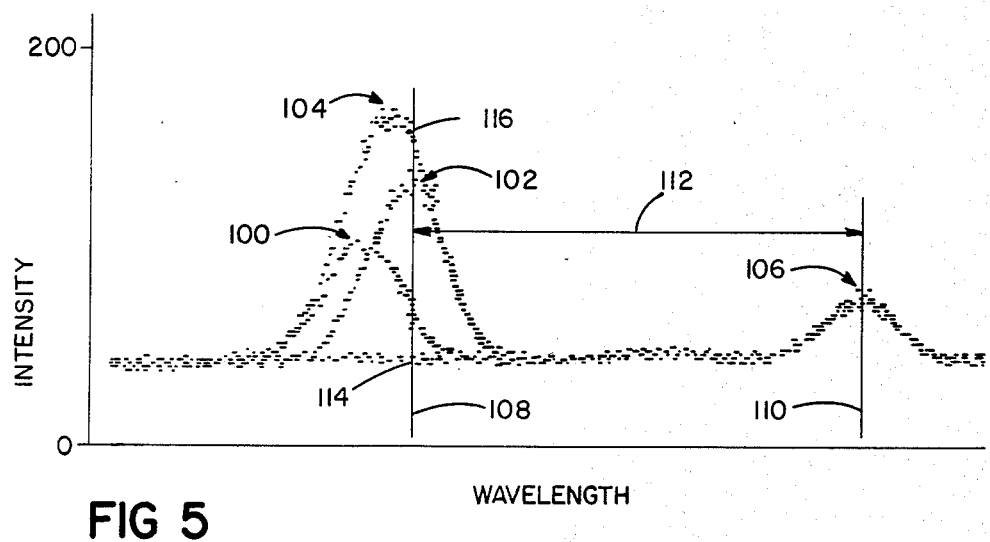
Figure 6:
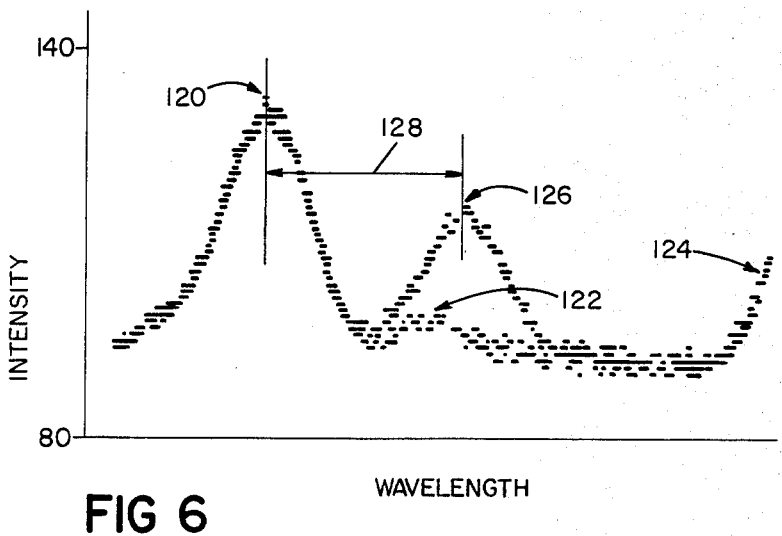
Figure 7:
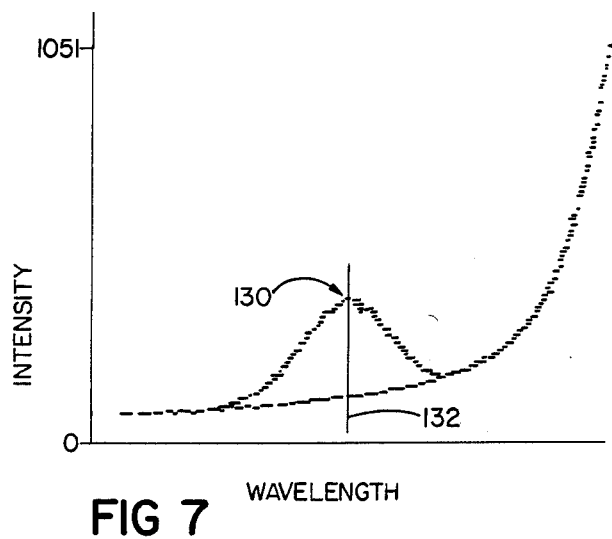
Figure 8:
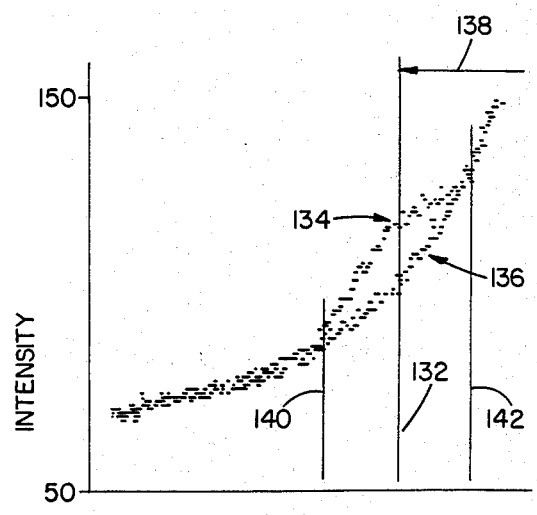

FIGS. 3 and 4 are sectional views taken along the lines 3—3 and 4—4 respectively of FIG. 2;

FIG. 5 shows a complex spectra of sample material that contains copper and phosphorus and illustrates a spectroanalytical measurement in accordance with the invention;

FIG. 6 illustrates a spectroanalytical measurement in accordance with the invention of a sample that contains one PPM lead and one-thousand PPM aluminum;

FIG. 7 illustrates a spectroanalytical measurement on a solution that contains twenty parts per million lead in one-thousand PPM aluminum; and FIG. 8 illustrates a spectroanalytical measurement in accordance with the invention on a solution that contains one part per million lead and one-thousand parts per million aluminum.

DESCRIPTION OF PARTICULAR EMBODIMENTS

Figure 1:
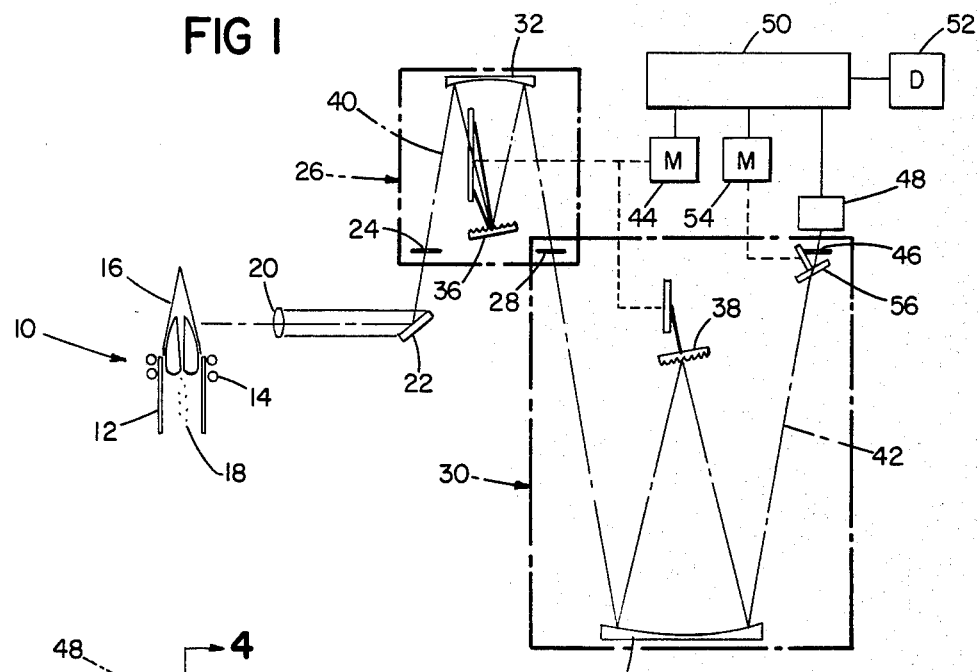
FIG. 1 is a diagram of a spectroanalysis system in accordance with the invention.

With reference to FIG. 1, the spectrometer system there diagrammatically illustrated includes an induction coupled plasma source 10 that has a tubular plasma chamber 12 surrounded by induction coil 14. Coil 14 is energized at a frequency of about 27.12 megahertz and excites a flow of argon gas to establish elongated plasma plume 16. The sample 18 to be analyzed is introduced in aerosol form into the plasma 16 and excited to spectroemissive levels.

Resulting radiation from plasma source 10 is focused by lens 20 and reflected by mirror 22 through entrance aperture 24 of 1/6 meter focal length filtering monochromator 26. The exit aperture 28 of filtering monochromator 26 is coincident with the entrance aperture of ⅓ meter focal length resolving monochromator 30. Each monochromator includes a spherical collimating mirror 32, 34 respectively, and a dispersing element 36, 38 respectively, in the form of a planar reflecting grating. Gratings 36, 38 are mounted for rotation about pivot axes that extend perpendicular to the planes of radiation beams 40, 42 and are driven in rotation by a common drive that includes stepper motor 44.

The exit beam 42 passes through exit slit 46 and is sensed by radiation detector 48 in the form of a photomultiplier tube and the resulting output signal is applied to a controller 50 with results being displayed by output device 52, for example a cathode ray tube (CRT) type device that produces a visual display of the type shown in FIGS. 5-8. Controller 50 also coordinates operation of grating drive motor 44 and stepper motor 54 that rotates refractor plate 56 for shifting the spectrum in exit beam 42 at exit slit 46. This spectroanalytical system is of the type shown in the Smith et al., U.S. Pat. No. 4,326,802. Further aspects of the resolving monochromator may be seen with reference to the sectional views of FIGS. 2, 3 and 4.

That resolving monochromator 30 includes a housing 60 with an entrance aperture 28 defined by adjustable slit disc structure 62. Diffraction grating 38 is blazed at five-thousand angstroms and is supported in holder 64 for rotation about grating axis 66 by a suitable support mechanism. Sine arm assembly 68 is fixed to holder 64 and includes follower 70 biased against the surface of glass plate 74 that is driven by nut structure 76 carried by precision lead screw shaft 78 that is mounted for rotation in bearing structures 80, 82 and driven by stepper motor 44. A similar sine arm assembly rotates the defraction grating 36 of the filtering monochromator, as described in further detail in the above referenced Smith et al., U.S. Pat. No. 4,326,802, such that the rotation of gratings 36, 38 are coordinated.

Refractor plate 56, a quartz plate one millimeter in thickness, is mounted on shaft 84 that is supported for rotation by bearings 86, 88. Secured to the lower end of shaft 84 is lever arm 90 that is coupled to screw shaft 92 of vernier linear stepper motor 54. Stepper motor 54 moves refractor plate 56 to shift the spectrum at exit slit 46 0.01 angstrom per step and provides a total excursion of 2.5 angstroms (250 steps).

FIG. 5 illustrates a CRT display at output 52 of spectroanalytical measurements on phosphorus-free sample material that contains ten parts per million copper (the copper peak 100 being at 214.897 nanometers); copper-free sample material that contains ten parts per million phosphorus (the phosphorus peak 102 of that sample being at 214.91 nanometers); and a third sample that contains ten parts per million copper and ten parts per million phosphorus producing an intensity (a peak 104 located between peaks 100 and 102); each sample contains ten parts per million tantalum (producing a peak 106 at 215.06 nanometers). As indicated in FIG. 5, the copper and phosphorus intensities combine in the third sample such that the resulting peak 104 is offset from the phosphorus wavelength 108 (214.91 nanometers) and the amount of phosphorus cannot be accurately determined by locating an intensity peak.

With reference to FIG. 5, in accordance with the invention, the specimen is spiked with ten parts per million tantalum, is excited and the monochromator scanning system is adjusted by peak sensing techniques to position the tantalum peak 106 (wavelength 110—215.06- nanometers—where there is no interference) at exit slit 46. The spectrum at the exit slit is then shifted 0.15 nanometers (wavelength offset 112) by rotating refractor plate 56 (150 steps of stepper motor 54) to 214.91 nanometers—the phosphorus wavelength 108 wavelength 108 and intensity measurements at that wavelength are made of a high standard, a blank (intensity 114) and the sample material to be analyzed (intensity 116). (In each analysis sequence, measurements are made at the wavelength of the element of interest on a high standard, a blank, and the sample material. The difference between the high standard and blank measurements provides a calibration value, and the proportion of the intensity generated by the sample material to the calibration value provides an indication of the quantity of the element of interest in the analyzed sample.) A copper correction factor is obtained by making similar high standard, blank and sample measurements at another copper wavelength (for example 324.7 nanometers) where there is no interference between phosphorus and copper, and that correction factor is used to correct the intensity measurement 116 to provide an accurate measurement of the amount of phosphorus in the sample.

Based on five replicate three-second integrations, by conventional techniques, the phosphorus in a copper free sample was determined to be 9.95 PPM, and with the side line reference method of the invention, the phosphorus content in that sample was determined to be 10.08 parts per million. When a 10 PPM copper (phosphorus free) sample was analyzed, a 6.5 PPM value was obtained in the conventional manner and a 2.2 PPM value was achieved with the side line index method of the invention. With five similar replicate three-second integrations with a sample that contained ten parts per million of copper and ten parts per million phosphorus, the conventional method gave a value of 13.8 PPM which when corrected by subtracting 6.5 PPM gave a resultant of 7.3 PPM (2.7 PPM below actual). By the method of the invention, a peak of 12.2 PPM was read and when corrected by subtracting 2.2 PPM gave a value of 10.0 PPM—the correct value. Thus, the method in accordance with the invention provided a significant increase in analysis accuracy as the reading is taken at the correct phosphorus wavelength rather than at an intensity peak.

The CRT display of FIG. 6 illustrates scans of a blank and a sample that contains one PPM aluminum. In the illustrated example, there are three adjacent hydroxyl peaks 120, 122 and 124. The aluminum signal at wavelength 126 is close to the small hydroxyl peak 122. When calibrating with the blank, a peak sensing system may calibrate at the hydroxyl peak 122 rather than proper aluminum wavelength 126. In accordance with the invention, a preliminary or reference measurement is made on the basis of the hydroxyl peak 120 and then the spectrum is shifted (as indicated at 128) to the aluminum wavelength where measurements of the high standard, blank and sample are made.

Other analyses are illustrated in FIGS. 7 and 8, FIG. 7 illustrating measurement on a solution that contains twenty parts per million lead and one-hundred parts per million aluminum; and FIG. 8 illustrating measurement on a solution that contains one part per million lead and one-thousand parts per million aluminum. As indicated by the intensity scale values, the display of FIG. 8 is expanded relative to the display of FIG. 7. The lead peak 130 at 220.35 nanometers (wavelength 132) can be identified accurately in the FIG. 7 display but the lead signal 134 in FIG. 8 lies on the slope 136 of the closely adjacent aluminum peak which swamps it out so that no peak is present at the lead wavelength 132. In accordance with the invention a reference measurement is made at the aluminum peak (220.463 nanometers) and then the spectrum is shifted (as indicated at 138) to the lead wavelength 132 (220.35 nanometers). An analysis measurement sequence of a high standard, a blank and the sample is made at that wavelength. Compensation for the aluminum interference may be obtained by making measurements of the background on either side of the lead peak, for example at wavelengths 140 and 142. If the background measurements are made at equal wavelength distances from the wavelength of the element of interest (132 in FIG. 8), a simple mean is employed. Otherwise, the measurements at wavelengths 140 and 142 are weighted to compensate for the unequal wavelength offsets.

While particular embodiments of the invention have been shown and described, various modifications will be apparent to those skilled in the art and therefore it is not intended that the invention be limited to the disclosed embodiments or to details thereof, and departures may be made therefrom within the spirit and scope of the invention.

What is claimed is:

1. A method of spectroanalytical analysis for measuring the quantity of an analyte constituent in sample material comprising the steps of
   exciting material to spectroemissive level,
   dispersing radiation from said excited material into a spectrum, positionally locating the output of a reference constituent of said material in said spectrum, said known constituent having a known wavelength offset from said analyte constituent in said spectrum, shifting said spectrum said known wavelength offset, exciting said sample material to spectroemissive level, dispersing radiation from said excited sample material into a spectrum, and measuring an output of said sample material spectrum at said known wavelength offset.

2. The method of claim 1 wherein said known wavelength offset is less than one nanometer.

3. The method of claim 1 wherein said radiation is dispersed by means of a reflection grating in a monochromator and said spectrum output of said reference constituent of said sample material is positionally located at the exit slit of said monochromator.

4. The method of claim 1 wherein said spectrum is shifted by means of a refractor plate.

5. The method of claim 4 wherein said refractor plate is adjacent the exit slit of a monochromator.

6. The method of claim 4 wherein said refractor plate is driven by a stepper motor to shift said spectrum, each step of said stepper motor shifting said spectrum less than 0.01 nanometer.

7. The method of claim 1 wherein the same material is excited to spectroemissive levels to positionally locate the output of said reference constituent in the spectrum and to measure said sample material spectrum at said known wavelength offset.

8. A scanning monochromator method of spectroanalytical analysis for measuring the quantity of an element of interest in sample material, said scanning monochromator including a source of the plasma emission type, structure defining an entrance aperture, structure defining an exit aperture, a radiation dispersing element for dispersing radiation from said source that passes through said entrance aperture into a spectrum, drive means for moving said dispersing element to cause said spectrum to scan past said exit aperture, and a radiation sensor responsive to radiation passing through said exit aperture comprising the steps of exciting material with said plasma source to spectroemissive level, directing radiation from said excited material through said entrance aperture for impingement on said dispersing element for dispersion into a spectrum, positionally locating the output of a reference constituent of said material in said spectrum at said exit aperture, said known constituent having a known wavelength offset from said element of interest in said spectrum, shifting said spectrum said known wavelength offset, exciting said sample material with said plasma source to spectroemissive level, directing radiation from said excited sample material through said entrance aperture for impingement on said dispersing element for dispersion into a spectrum, and measuring the radiation intensity with said radiation sensor of said sample material spectrum at said known wavelength offset to determine the quantity of said element of interest in said sample material.

9. The method of claim 8 wherein said dispersing element is a reflection grating and said monochromator further includes a refractor plate adjacent said exit aperture of said monochromator and a stepper motor drive for rotating said refractor plate, said spectrum being shifted said known wavelength offset by rotation of said refractor plate by said stepper motor, each step of said stepper motor shifting said spectrum at said exit aperture less than 0.01 nanometer.

10. The method of claim 9 wherein said known wavelength offset is less than one nanometer.

11. The method of claim 10 wherein the same material is excited to spectroemissive levels to positionally locate the output of said reference constituent in the spectrum and to measure said sample material spectrum at said known wavelength offset.

* * * * *